United States Patent
Vautravers et al.

(10) Patent No.: US 10,144,691 B2
(45) Date of Patent: Dec. 4, 2018

(54) PROCESS FOR PREPARING 1-[(1R,4R/S,8S)-10,10-DIMETHYL-7-METHYLENE-4-BICYCLO[6.2.0]DECANYL]ETHANONE

(71) Applicant: BASF SE, Ludwigshafen (DE)

(72) Inventors: Nicolas Vautravers, Mannheim (DE); Joaquim Henrique Teles, Waldsee (DE); Ralf Pelzer, Fürstenberg (DE); Daniel Schneider, Frankenthal (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/537,128

(22) PCT Filed: Dec. 18, 2015

(86) PCT No.: PCT/EP2015/080389
§ 371 (c)(1),
(2) Date: Jun. 16, 2017

(87) PCT Pub. No.: WO2016/097239
PCT Pub. Date: Jun. 23, 2016

(65) Prior Publication Data
US 2018/0265443 A1 Sep. 20, 2018

(30) Foreign Application Priority Data
Dec. 19, 2014 (EP) .................................. 14199401

(51) Int. Cl.
*C07C 45/28* (2006.01)
*C07C 45/82* (2006.01)

(52) U.S. Cl.
CPC .............. *C07C 45/28* (2013.01); *C07C 45/82* (2013.01); *C07C 2602/26* (2017.05)

(58) Field of Classification Search
CPC ...... C07C 45/28; C07C 45/82; C07C 2602/26
See application file for complete search history.

(56) References Cited

U.S. PATENT DOCUMENTS

| 7,449,606 B2 | 11/2008 | Teles et al. |
| 7,838,705 B2 | 11/2010 | Teles et al. |
| 8,420,866 B2 | 4/2013 | Teles et al. |
| 8,461,392 B2 | 6/2013 | Teles et al. |

FOREIGN PATENT DOCUMENTS

| JP | H11035969 A | 2/1999 |
| JP | H11071312 A | 3/1999 |
| WO | WO-2005030689 A2 | 4/2005 |
| WO | WO-2005030690 A2 | 4/2005 |
| WO | WO-2010023211 A2 | 3/2010 |
| WO | WO-2010076182 A1 | 7/2010 |
| WO | WO-2016097238 A1 | 6/2016 |

OTHER PUBLICATIONS

Collado, I., et al., "Recent advances in the chemistry of caryophyllene", Natural Product Reports, vol. 15, (1998), pp. 187-204.
Hermans, I., et al., "Diazo chemistry controlling the selectivity of olefin ketonisation by nitrous oxide", Physical Chemistry Chemical Physics, vol. 9, No. 31, (2007), pp. 4269-4274.
International Search Report for PCT/EP2015/080388 dated Feb. 17, 2016.
International Search Report for PCT/EP2015/080389 dated May 27, 2016.
Matsubara, Y., et al., "Reinvestigation of oxidation products of β-Caryophyllene with lead tetraacetate", Nippon Nōgeikagaku Kaishi, vol. 59, No. 1, (1985), pp. 19-24 (in German) with Database Caplus, Accession No. 1985-560705, XP-002739759 (in English).
Sköld, M., et al., "The fragrance chemical b-caryophyllene—air oxidation and skin sensitization", Food and Chemical Toxicology, vol. 44, (2006), pp. 538-545.
Starkon, K.A., et al., "Liquid Phase Oxidation of Alkenes with Nitrous Oxide to Carbonyl Compounds", Advanced Synthesis Catalysis, vol. 346, No. 2-3, (2004), pp. 268-274.
Uschida, T., et al., "Structures of Two Novel Sesquiterpenoids Formed by the Lead Tetraacetate Oxidation of b-Caryophyllene", Agricultural and Biological Chemistry, vol. 53, No. 11, (1989), pp. 3011-3015.
Written Opinion of the International Searching Authority for PCT/EP2015/080388 dated Feb. 17, 2016.
Written Opinion of the International Searching Authority for PCT/EP2015/080389 dated May 27, 2016.

*Primary Examiner* — Sikarl A Witherspoon
(74) *Attorney, Agent, or Firm* — Drinker Biddle & Reath LLP

(57) ABSTRACT

The present invention relates to a process for preparing 1-[(1R,4R/S,8S)-10,10-dimethyl-7-methylene-4-bicyclo[6.2.0]decanyl]ethanone.

6 Claims, No Drawings

PROCESS FOR PREPARING 1-[(1R,4R/S,8S)-10,10-DIMETHYL-7-METHYLENE-4-BICYCLO[6.2.0]DECANYL]ETHANONE

CROSS-REFERENCE TO RELATED APPLICATIONS

This application is a national stage application (under 35 U.S.C. § 371) of PCT/EP2015/080389, filed Dec. 18, 2015, which claims benefit of European Application No. 14199401.2, filed Dec. 19, 2014, both of which are incorporated herein by reference in their entirety.

The present invention relates to a process for preparing 1-[(1R,4R/S,8S)-10,10-dimethyl-7-methylene-4-bicyclo[6.2.0]decanyl]ethanone.

BACKGROUND OF THE INVENTION

Fragrances are of great interest especially in the field of cosmetics and also laundry and cleaning detergents. Fragrances of natural origin are mostly expensive, often limited in their available amount and, on account of fluctuations in environmental conditions, are also subject to variations in their content, purity etc. To circumvent these undesirable factors, it is therefore of great interest, by way of example, to chemically modify readily available natural substances, e.g. readily available fragrances of natural origin, to create substances, which have organoleptic properties that resembles more expensive natural fragrances or which have novel and interesting organoleptic profiles. Such "semi-synthetic" substances can, by way of example, be used as substitutes for purely natural substances on account of their odor, where substitute and natural substance do not necessarily have to have a chemical-structural similarity.

Caryophyllene and its analogs are known fragrance chemicals. Caryophyllene is a natural product, which can readily be isolated from clove oil. Some of its oxidation products are also described in the state of the art.

There is a constant need for novel processes, e.g. by making use of mild oxidation reactions, to improve the production of aroma chemicals with advantageous sensory properties.

Starokon et al., Adv. Synth. Catal. 2004, Vol. 346, pp. 268-274, describe the oxidation of 1-methyl cyclohexene with $N_2O$. 1-methyl cyclohexene was oxidized in substance at 250° C. under 25 bar of $N_2O$ for 12 hours. The conversion of 1-methyl-cyclohexene in this reaction was 33% and a product mixture containing 2-methylcyclohexanone as the main product (44% selectivity), methyl cyclopentyl ketone (34% selectivity), methyl-pent-4-en-1-yl-ketone (5% selectivity) and 5-heptenal (2-3% selectivity) was obtained.

Hermans et al., Phys. Chem. Chem. Phys., 2007, Vol. 9, pp. 4269-4274, describe a similar oxidation reaction of 1-methyl cyclohexene with $N_2O$, which gave the same reaction products in almost identical selectivities. They also observed a very low reaction rate for this oxidation reaction.

Beta-caryophyllene ((1R,4E,9S)-4,11,11-trimethyl-8-methylene-bicyclo[7.2.0]undec-4-ene) and its analogs are known fragrance chemicals. Several of its oxidation products are also described in the state of the art.

Sköld et al., Food and Chemical Toxicology, 2006, Vol. 44, pp. 538-545, describe the air oxidation of the fragrance chemical beta-caryophyllene to caryophyllene oxide and its allergenic activity.

Collado et al., Nat. Prod. Reports, 1998, Vol. 15, pp. 187-204, describe the physical properties and reactivity of beta-caryophyllene in detail, including its oxidation products that are obtained from various oxidation reactions.

Matsubara et al., Nippon Nogei Kagaku Kaishi, 1985, Vol. 59, Nr. 1, pp. 19-24, and Uchida et al., Agric. Biol. Chem., 1989, Vol. 53, Issue 11, pp. 3011-3015, describe the oxidation of beta-caryophyllene with lead tetraacetate and the analytical characterization of the obtained oxidation products. Besides 11 other compounds, they identified 1-[(1R,4R,8S)-10,10-dimethyl-7-methylene-4-bicyclo[6.2.0]decanyl]ethanone and 1-[(1R,4S,8S)-10,10-dimethyl-7-methylene-4-bicyclo[6.2.0]decanyl]ethanone in the oxidation product mixture. Specifically, the oxidation reaction is performed by reacting beta-caryophyllene with lead(IV) acetate in stoichiometric quantities, upon which 1-[(1R,4R,8S)-10,10-dimethyl-7-methylene-4-bicyclo[6.2.0]decanyl]ethanone and 1-[(1R,4S,8S)-10,10-dimethyl-7-methylene-4-bicyclo[6.2.0]decanyl]ethanone were obtained in a selectivity of 10.2% and 9.9%, respectively. Furthermore, they propose the potential use of these oxidation products in perfumes, due to their mildly woody odor.

SUMMARY OF THE INVENTION

It was an object of the present invention to provide an improved process for the effective preparation of 1-[(1R,4R/S,8S)-10,10-dimethyl-7-methylene-4-bicyclo[6.2.0]decanyl]ethanone. Furthermore, the process should provide the desired product in high yield and selectivity without the use of toxic and/or expensive reagents.

It was surprisingly found, that 1-[(1R,4R/S,8S)-10,10-dimethyl-7-methylene-4-bicyclo[6.2.0]decanyl]ethanone can be prepared in high yield and selectivity by reacting (1R,4E,9S)-4,11,11-trimethyl-8-methylene-bicyclo[7.2.0]undec-4-ene (beta-caryophyllene) with $N_2O$. Accordingly, the invention relates to a process for producing 1-[(1R,4R/S,8S)-10,10-dimethyl-7-methylene-4-bicyclo[6.2.0]decanyl]ethanone or a mixture of its stereoisomers predominantly containing the 4R-isomer, which comprises reacting (1R,4E,9S)-4,11,11-trimethyl-8-methylene-bicyclo[7.2.0]undec-4-ene with $N_2O$.

The present process exhibits the following advantages:

- 1-[(1R,4R/S,8S)-10,10-dimethyl-7-methylene-4-bicyclo[6.2.0]decanyl]ethanone can be synthetically produced in high selectivities by using the cheap and readily obtainable starting material (1R,4E,9S)-4,11,11-trimethyl-8-methylene-bicyclo[7.2.0]undec-4-ene, which is also termed beta-caryophyllene.

- 1-[(1R,4R/S,8S)-10,10-dimethyl-7-methylene-4-bicyclo[6.2.0]decanyl]ethanone can be synthetically produced without having to use expensive and/or toxic reagent such as lead(IV) acetate.

- The processes for producing 1-[(1R,4R/S,8S)-10,10-dimethyl-7-methylene-4-bicyclo[6.2.0]decanyl]ethanone is simple and efficient. 1-[(1R,4R/S,8S)-10,10-dimethyl-7-methylene-4-bicyclo[6.2.0]decanyl]ethanone can therefore be provided without difficulty on a large industrial scale.

DETAILED DESCRIPTION

1-[(1R,4R/S,8S)-10,10-dimethyl-7-methylene-4-bicyclo[6.2.0]decanyl]ethanone is a compound of the following formula (I):

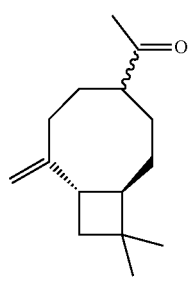
(I)

It is apparent from formula (I) that carbon atom of the 4-position, which carries the acetyl group, may have (R)- or (S)-configuration. Hence, 1-[(1R,4R/S,8S)-10,10-dimethyl-7-methylene-4-bicyclo[6.2.0]decanyl]ethanone can be present in the form either of the (1R,4R,8S)-isomer 1-[(1R,4R,8S)-10,10-dimethyl-7-methylene-4-bicyclo[6.2.0]decanyl] ethanone, hereinafter also termed 4R-isomer, or of the (1R,4S,8S)-isomer 1-[(1R,4S,8S)-10,10-dimethyl-7-methylene-4-bicyclo[6.2.0]decanyl]ethanone, hereinafter termed 4S-isomer, respectively, or in the form of mixtures of the (1R,4R,8S)-isomer and the (1R,4S,8S)-isomer, hereinafter termed 4R/4S-isomer mixtures.

Using the process according to the present invention, the (1R,4R,8S)- and (1R,4S,8S)-stereoisomer of 1-[(1R,4R/S,8S)-10,10-dimethyl-7-methylene-4-bicyclo[6.2.0]decanyl]-ethanone as well as mixtures of these stereoisomers can be prepared. The term "1-[(1R,4R/S,8S)-10,10-dimethyl-7-methylene-4-bicyclo[6.2.0]decanyl]ethanone" encompasses both the pure (1R,4R,8S)-isomer and (1R,4S,8S)-isomer, as well as mixtures, where these stereoisomers are present in equal amounts or wherein one of these stereoisomers is present in excess.

Frequently, the present process provides 1-[(1R,4R/S,8S)-10,10-dimethyl-7-methylene-4-bicyclo[6.2.0]decanyl]ethanone as 4R/4S-isomer mixtures.

More frequently, the present process provides 1-[(1R,4R/S,8S)-10,10-dimethyl-7-methylene-4-bicyclo[6.2.0]decanyl]ethanone in the form of a mixture of 4R/4S-stereoisomers thereof, which predominantly contains either the 4R-isomer or the 4S-isomer. More specifically, in these mixtures, the 4R- or 4S-isomer of 1-[(1R,4R/S,8S)-10,10-dimethyl-7-methylene-4-bicyclo[6.2.0]decanyl]-ethanone is present in an amount of at least 55% by weight, in particular of at least 65% by weight, based on the total amount of the 4R- and 4S-isomers of 1-[(1R,4R/S,8S)-10,10-dimethyl-7-methylene-4-bicyclo[6.2.0]decanyl]ethanone.

In a particular embodiment of the present process, 1-[(1R,4R/S,8S)-10,10-dimethyl-7-methylene-4-bicyclo[6.2.0]decanyl]ethanone is obtained in the form of a mixture of 4R/4S-stereoisomers thereof, which predominantly contains the 4R-isomer. More specifically, in these mixtures, the 4R-isomer of 1-[(1R,4R/S,8S)-10,10-dimethyl-7-methylene-4-bicyclo[6.2.0]decanyl]-ethanone is present in an amount of at least 55% by weight, in particular of at least 65% by weight, based on the total amount of the 4R- and 4S-isomers of 1-[(1R,4R/S,8S)-10,10-dimethyl-7-methylene-4-bicyclo[6.2.0]decanyl]ethanone. Even more specifically, in these mixtures, the 4R-isomer of 1-[(1R,4R/S,8S)-10,10-dimethyl-7-methylene-4-bicyclo[6.2.0]decanyl]-ethanone is present in an amount of at least 90% by weight, based on the total amount of the 4R- and 4S-isomers of 1-[(1R,4R/S,8S)-10,10-dimethyl-7-methylene-4-bicyclo[6.2.0]decanyl]ethanone.

In a special embodiment of the present process, 1-[(1R,4R/S,8S)-10,10-dimethyl-7-methylene-4-bicyclo[6.2.0]decanyl]ethanone or the 4R/4S-stereoisomer mixtures thereof, as defined above, are obtained in a purity of at least 80%, in particular at least 90%.

The preferred embodiments mentioned above may be combined arbitrarily with one another.

Accordingly, in a particular embodiment of the present process, 1-[(1R,4R/S,8S)-10,10-dimethyl-7-methylene-4-bicyclo[6.2.0]decanyl]ethanone is obtained in the form of a mixture of 4R/4S-stereoisomers thereof, which contain the 4R-isomer in an amount of at least 55% by weight, based on the total amount of the 4R- and 4S-isomers of 1-[(1R,4R/S,8S)-10,10-dimethyl-7-methylene-4-bicyclo[6.2.0]decanyl]ethanone, and where said mixture has a purity of at least 80%.

The invention provides a process for preparing 1-[(1R,4R/S,8S)-10,10-dimethyl-7-methylene-4-bicyclo[6.2.0]decanyl]ethanone, as defined above, which comprises reacting (1R,4E,9S)-4,11,11-trimethyl-8-methylene-bicyclo[7.2.0]undec-4-ene (beta-caryophyllene) with $N_2O$.

The oxidation of an olefinic C=C-double bond in olefinically unsaturated organic compounds with $N_2O$ is principally known in the art. The oxidation of beta-caryophyllene with $N_2O$ may be performed by analogy to known methods, e.g. by analogy to the methods described in the prior art as discussed above or by Starokon et al, Adv. Synth. Catal. 2004, Vol. 346, pp. 268-274, Romanenko et al., Russ. Chem. Bull. Int. Ed. 2007, Vol. 56, pp. 1239-43 (Oxidation von Terpenen mit $N_2O$) as well as WO 2005/030690, WO 2005/030689, WO 2010/023211 and WO 2010/0076182 (technical oxidation of olefins with $N_2O$).

To this end, beta-caryophyllene in the form of liquid phase is heated in the presence of $N_2O$. To increase the solubility of $N_2O$ in the liquid phase, the reaction is preferably performed at elevated pressure.

The reaction is in particular performed at a pressure, in particular at a $N_2O$ pressure, in the range of 5 to 325 bar, preferably in the range of 20 to 250 bar, especially in the range from 60 to 200 bar.

The oxidation can be designed to take place either continuously or batchwise, preference being given here to the continuous design of the process. The batchwise oxidation can be conducted in a reaction apparatus conventionally used for this purpose, e.g. a stirred reactor. It is preferable that the oxidation according to the present invention is carried out continuously, e.g. in a tube reactor or in a cascade of at least three back-mixed reactors. The reactors can be operated isothermal or adiabatic.

Typically, the reaction is performed without adding a catalyst.

The oxidation reaction is usually carried out in the temperature range from 100 to 300° C., preferably from 130 to 290° C., in particular in the range from 150 to 280° C.

The oxidation reaction can be carried out in bulk, i.e. in the absence of any added solvent or in the presence of one or more organic solvents.

If the oxidation reaction is carried out in the presence of an organic solvent, it is preferred that the organic solvent is inert under the reaction conditions. Preferred inert organic solvents are, by way of example, aliphatic or alicyclic hydrocarbons, in particular alkanes and cycloalkanes having 5 to 12 carbon atoms, halogenated aliphatic hydrocarbons, and aromatic and substituted aromatic hydrocarbons, and aliphatic or alicyclic ethers. Examples of inert solvents are aliphatic hydrocarbons, such as pentane, hexane, heptane, ligroin, petrol ether, cyclohexane, halogenated hydrocarbons, such as dichloromethane, trichloromethane, tetrachloromethane or dichloroethane, aromatics, such as benzene, toluene, xylenes, chlorobenzene, dichlorobenzenes, ethers such as methyl-tert.-butylether, dibutyl ether, tetrahydrofurate, 1,4-dioxane, 1,2-dimethoxyethane and mixtures thereof.

If the oxidation reaction is carried out in the presence of an inert organic solvent, the amount of the solvent in the reaction mixture is preferably less than 90% by weight, preferably less than 80% by weight, based on the amount of beta-caryophyllene.

In particular, the oxidation is carried out in the absence of an inert organic solvent.

The oxidation reaction can take place in the absence of or in the presence of an inert gas. The expression inert gas generally means a gas which under the prevailing reaction conditions does not enter into any reactions with the starting materials, reagents, or solvents participating in the reaction, or with the resultant products. Examples of inert gases are $N_2$, $CO_2$ and noble gases like He, Ne, Ar, Kr and Xe. It is preferable that the dimerization reaction takes place without addition of any inert gas.

In particular, the molar ratio of $N_2O$ to beta-caryophyllene used in the oxidation reaction is in the range of 1:50 to 10:1, preferably in the range of 1:20 to 5:1, in particular in the range of 1:10 to 1:1

Preferable, the reaction conditions and in particular the amount of $N_2O$, the reaction pressure, reaction temperature and the reaction time is chosen such that the conversion rate of beta-caryophyllene is in the range of 10 to 98%, in particular in the range of 30 to 90% or in the range of 50 to 85%.

The process of the present invention provides 1-[(1R,4R/S,8S)-10,10-dimethyl-7-methylene-4-bicyclo[6.2.0]decanyl]ethanone in good yield and selectivity. Surprisingly, $N_2O$ preferentially reacts with the trisubstituted endocyclic double bond of beta-caryophyllene. In view of the low conversion rates for the oxidation of 1-methyl cyclohexane with $N_2O$ described in the prior art, a skilled person would have expected, that $N_2O$ would also react with the exocyclic double bond at comparable reaction rates. However, the main observed reaction stems from the [2+3]-cycloaddition of $N_2O$ to the trisubstituted endocyclic double bond followed by the elimination of $N_2$ and a rearrangement of the carbon skeleton.

Generally, the crude product mixture obtained by the process according to the present invention may comprise further reaction products. In particular, the crude product mixture may contain, in addition to the main product of formula I, further products of the general formulae (II) to (V).

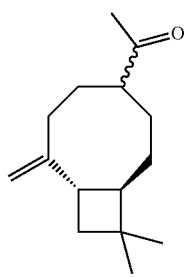

(I)

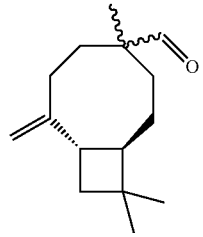

(II)

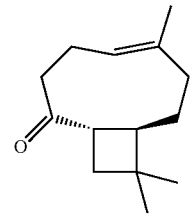

(III)

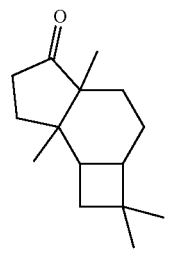

(IV)

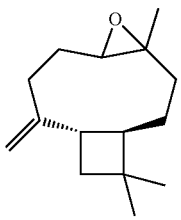

(V)

Surprisingly, the ketone of formula (VI),

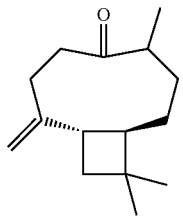

(VI)

which, by analogy to the known oxidation of 1-methyl cyclohexene using $N_2O$, might be expected to be the major oxidation product of beta-caryophyllene, is typically not found among the reaction products in detectable amounts. The detection limit of the gas-chromatographic analysis system used is estimated to be about 10 wt.-ppm.

Compound (II) has been described previously as one of the products formed by hydrolysis of caryophyllene oxide (Yang et al., J. Nat. Prod. 1994, Vol. 57, pp. 514). The nor-ketone (III) is also a known product (compound 9 of Collado et al., Nat. Prod. Reports 1998, Vol. 15, pp. 187-204). The tricyclus (IV) is also known in the literature (compounds 16 and 17 in Barrero et al., Eur. J. Org. Chem.

2006, pp. 3434-3441). Caryophyllene oxide (V) is also known in the literature (Siegel et al., Org. Biomol. Chem. 2012, Vol. 10, pp. 383-393).

The process of the present invention may further comprise the purification of 1-[(1R,4R/S,8S)-10,10-dimethyl-7-methylene-4-bicyclo[6.2.0]decanyl]ethanone, e.g. by distillation.

Preferred distillation devices for the purification of 1-[(1R,4R/S,8S)-10,10-dimethyl-7-methylene-4-bicyclo[6.2.0]decanyl]ethanone are for example distillation columns, such as tray columns optionally equipped with bubble cap trays, sieve plates, sieve trays, packages or filler materials, or spinning band columns, such as thin film evaporators, falling film evaporators, forced circulation evaporators, Sambay evaporators, etc. and combinations thereof. Especially preferred distillation devices for the purification of 1-[(1R,4R/S,8S)-10,10-dimethyl-7-methylene-4-bicyclo[6.2.0]decanyl]ethanone are distillation columns, in particular packed columns, e.g. columns packed with high efficiency structured packing, and spinning band columns.

After destillative purification 1-[(1R,4R/S,8S)-10,10-dimethyl-7-methylene-4-bicyclo[6.2.0]decanyl]ethanone can typically be obtained in high purity, e.g. in a purity of at least 80%. Generally, 1-[(1R,4R/S,8S)-10,10-dimethyl-7-methylene-4-bicyclo[6.2.0]decanyl]ethanone is obtained as a non-racemic mixture of its 4R- and 4S-stereoisomers as defined above.

Generally, the starting material beta-caryophyllene (CAS-No. 87-44-5) is isolated from clove oil on technical scales and can be readily obtained from commercially sources.

1-[(1R,4R/S,8S)-10,10-dimethyl-7-methylene-4-bicyclo[6.2.0]decanyl]ethanone possesses advantageous sensory properties, in particular a pleasant odor. More specifically, 1-[(1R,4R/S,8S)-10,10-dimethyl-7-methylene-4-bicyclo[6.2.0]decanyl]ethanone exhibits an intensive odor of largely ambery, woody, powdery-sweet and feminine character.

Intensive odor impressions are to be understood as meaning those properties of aroma chemicals which permit a precise perception even in very low gas-space concentrations. The intensity can be ascertained via a threshold-value determination. A threshold value is the concentration of a substance in the relevant gas space at which an odor impression can just still be perceived by a representative test panel, although it no longer has to be defined. The substance class known as probably one of the most odor-intensive, i.e. those with very low threshold values, are thiols, whose threshold value is in the ppb/m$^3$ range. It is the aim of the search for new aroma chemicals to find substances with the lowest possible threshold value in order to permit the lowest possible use concentration. The closer one comes to this target, the more one talks of "intensive" odor substances or aroma chemicals.

"Pleasant odors" or "Advantageous sensory properties" are hedonic expressions which describe the niceness and preciseness of an odor impression conveyed by an aroma chemical.

"Niceness" and "preciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also describe the odor of musk or sandalwood. "Preciseness" generally refers to a spontaneously brought about sensory impression which—for the same test panel—brings about a reproducibly identical reminder of something specific.

For example, a substance can have an odor which is spontaneously reminiscent of that of an "apple": the odor would then be precisely of "apples". If this apple odor were very pleasant because the odor is reminiscent, for example, of a sweet, fully ripe apple, the odor would be termed "nice". However, the odor of a typically tart apple can also be precise. If both reactions arise upon smelling the substance, in the example thus a nice and precise apple odor, then this substance has particularly advantageous sensory properties.

Due to its pleasant odor, 1-[(1R,4R/S,8S)-10,10-dimethyl-7-methylene-4-bicyclo[6.2.0]decanyl]ethanone or a mixtures of its 4R/4S-stereoisomers, as defined above, which are obtained by the process of the present invention, can advantageously be used in compositions, which typically comprise at least one aroma compound, i.e. at least one fragrance and/or flavoring. Such compositions include, for example, laundry detergents, fabric detergents, cosmetic preparations, other fragranced hygiene articles, such as diapers, sanitary towels, armpit pads, paper towels, wet wipes, toilet paper, pocket tissues, and the like, foods, food supplements, examples being chewing gums or vitamin products, fragrance dispensers, examples being room air fresheners, perfumes, pharmaceutical preparations, and also crop protection products.

Typically, these compositions are formulated by incorporating 1-[(1R,4R/S,8S)-10,10-dimethyl-7-methylene-4-bicyclo[6.2.0]decanyl]ethanone or the above defined mixtures of its 4R/4S-stereoisomers, optionally together with one or more other aroma compounds, into an existing preparation, which before comprises no aroma compound or which before comprises one or more other aroma compound different from 1-[(1R,4R/S,8S)-10,10-dimethyl-7-methylene-4-bicyclo[6.2.0]decanyl]ethanone. Such compositions generally further comprise a carrier, which may be a compound, a compound mixture or other additives, which have no or no noticeable sensory properties. The carrier may as well be a compound or an additive having noticeable sensory properties, or a compound mixture comprising one or more other aroma compounds different from compounds 1-[(1R,4R/S,8S)-10,10-dimethyl-7-methylene-4-bicyclo[6.2.0]decanyl]ethanone and optionally one or more compounds having no or no noticeable sensory properties.

In these compositions, 1-[(1R,4R/S,8S)-10,10-dimethyl-7-methylene-4-bicyclo[6.2.0]decanyl]ethanone, in particular a mixture of its stereoisomers, where the 4R-isomer is present in excess, are usually applied in amounts customary for formulation auxiliaries. Suitable amount of 1-[(1R,4R/S,8S)-10,10-dimethyl-7-methylene-4-bicyclo[6.2.0]decanyl]ethanone are in the range of 0.001 to 50% by weight, in particular in the range of 0.01 to 20% by weight, especially in the range of 0.1 to 10% by weight, based on the total weight of the composition.

1-[(1R,4R/S,8S)-10,10-dimethyl-7-methylene-4-bicyclo[6.2.0]decanyl]ethanone, obtained by the process of the present invention, is especially suitable for use in laundry detergents and fabric detergents, in cosmetic preparations and in other fragranced hygiene articles. In particular, 1-[(1R,4R/S,8S)-10,10-dimethyl-7-methylene-4-bicyclo[6.2.0]decanyl]ethanone is suitable for use in cosmetic preparations such as perfumes.

The intensively and precisely smelling 1-[(1R,4R/S,8S)-10,10-dimethyl-7-methylene-4-bicyclo[6.2.0]decanyl]ethanone, obtained by the process of the present invention, is preferably suitable for use as fragrance. Suitable fields of application are all applications in which a certain odor is desired, whether it is to mask more unpleasant odors or to generate a certain odor or certain odor notes in a targeted manner.

Therefore, 1-[(1R,4R/S,8S)-10,10-dimethyl-7-methylene-4-bicyclo[6.2.0]decanyl]ethanone, obtained by the present process, is further suitable for the preparation of fragrance containing composition and/or a fragrance material, which contains 1-[(1R,4R/S,8S)-10,10-dimethyl-7-methylene-4-bicyclo[6.2.0]decanyl]ethanone and a carrier material.

The total concentration of 1-[(1R,4R/S,8S)-10,10-dimethyl-7-methylene-4-bicyclo[6.2.0]decanyl]ethanone in such fragrance containing composition and/or fragrance material is not particularly limited. It can be over a wide range, depending on the purpose of their use. Generally, amounts that are customary for fragrances are used. Suitable amounts of 1-[(1R,4R/S,8S)-10,10-dimethyl-7-methylene-4-bicyclo[6.2.0]decanyl]-ethanone in the fragrance containing composition and/or the fragrance material are typically in the range from 0.001 to 20% by weight, in particular in the range from 0.01 to 10% by weight.

The carrier material may be a compound, a compound mixture or other additives having the properties as defined above. Suitable carrier materials may comprise liquid or oil-based carrier materials as well as wax-like or solid carrier materials.

Suitable liquid or oil-based carrier materials are for example selected from alcohols, such as ethanol, water, aliphatic diols and polyols having melting temperatures below 20° C., such as ethylene glycol, glycerol, diglycerol, propylene glycol, dipropylene glycol, cyclic siloxanes (silicon fluids), such as hexamethylcyclotrisiloxane or decamethylcyclopentasiloxane, plant-oils, such as fractionated coconut-oil, or esters of fatty alcohols having melting temperatures below 20° C., such as myristyl acetate or myristyl lactate, and alkyl esters of fatty acids having melting temperatures below 20° C., such as isopropyl-myristate.

Suitable wax-like or solid carrier materials are for example selected from fatty alcohols having melting temperatures above 20° C., such as myristyl alcohol, stearyl alcohol or cetyl alcohol, polyols and esters of fatty alcohol having melting temperatures above 20° C., synthetic petroleum derived waxes, such as paraffin waxes, water insoluble porous minerals, such as silica, silicates, for example talc, microporous aluminasilicate minerals (zeolites), clay minerals, for example bentonite, or phosphates for example sodium tripolyphosphate, paper, cardboard, wood, nonwoven of rayon staple fibers or fiber-fleeces.

Suitable carrier materials are for example also selected from water-soluble polymers, such as polyacrylic acid esters or quaternized polyvinyl pyrrolidone or water-alcohol-soluble polymers, such as specific thermoplastic polyesters and polyamides. The polymeric carrier material can be present in different forms, for example in form of a gel, a paste, or water insoluble solid particles, such as microcapsules or friable coatings.

Depending on the purpose of use, the carrier materials may further comprise other additives or auxiliaries, for example surfactants or mixtures of surfactants, viscosifiers, such as polyethylene glycols with a molecular weight of 400 to 20'000 Da, lubricates, binding or agglomerating agents, such as sodium silicate, dispersing agents, detergent builder salts, filler salts, pigments, dyes, optical brighteners, anti-redeposition agents and the like.

Typical applications of such compositions and/or the fragrance materials are in the field of laundry and cleaning detergents, preparations of fragrances for the human or animal body, for rooms such as kitchens, wet rooms, automobiles or heavy goods vehicles, for real or artificial plants, for clothing, for shoes and shoe insoles, for items of furniture, for carpets, for air humidifiers and air fresheners, for cosmetics such as perfumes. 1-[(1R,4R/S,8S)-10,10-dimethyl-7-methylene-4-bicyclo[6.2.0]decanyl]ethanone, which is obtained by the process of the present invention, is also particularly suitable for the preparation of odorant combinations which comprise 1-[(1R,4R/S,8S)-10,10-dimethyl-7-methylene-4-bicyclo[6.2.0]decanyl]ethanone or the non-racemic mixture thereof as component A and at least one further compound known as an odorant or aroma substance, as component B, such as, for example, one or more of the following compounds B1 to B11:

B1: methyl dihydrojasmonate (e.g. hedione),

B2: 4,6,6,7,8,8-hexamethyl-1,3,4,6,7,8-hexahydrocyclopenta[g]benzopyran (e.g. Galaxolide™), B3: 2-methyl-3-(4-tert-butylphenyl)propanal (Lysmeral™), B4: 2-methyl-3-(4-isopropylphenyl)propanal (cyclamenaldehyde), B5: 2,6-dimethyl-7-octen-2-ol (dihydromyrcenol), B6: 3,7-dimethyl-1,6-octadien-3-ol (linalool), B7: 3,7-dimethyl-trans-2,6-octadien-1-ol (geraniol), B8: 2,3,8,8-tetramethyl-1,2,3,4,5,6,7,8-octahydro-2-naphthalenyl methyl ketone (Iso E Super™), B9: alpha-hexylcinnamaldehyde, B10: 3,7-dimethyl-6-octen-1-ol (citronellol), B11: alpha- or beta- or delta-damascone.

Suitable formulations of odor substances are, for example, the formulations disclosed in JP 11-071312 A, paragraphs [0090] to [0092]. The formulations from JP 11-035969 A, paragraphs [0039] to [0043] are also likewise suitable.

EXAMPLES

I) Gas Chromatographic Analysis

GC-System and Separation Method:

GC-system: Agilent 7890A

GC-Column: HP-5 (60 m (Length), 0.32 mm (ID), 1.0 μm (Film))

Temperature program: 100° C. to 225° C. in 5° C./min, 10 minutes at 225° C., 225° C. to until 280° C. in 5° C./min.

II) Production Examples

Example II.1

Oxidation of Beta-Caryophyllene in Toluene at 230° C. with $N_2O$ (40 Bar)

A 300 mL autoclave is charged with 30.0 g beta-caryophyllene (88 wt.-% obtained from Aldrich Chemicals) in 70.0 g toluene and flushed 3 times with $N_2$ (50 bar). The vessel is then pressurized with $N_2O$ (40 bar) at room temperature. The magnetic stirring is turned on and the autoclave heated to the reaction temperature (230° C.) for 3 hours. During reaction the pressure in the autoclave was about 70-75 bar. After cooling to room temperature and slow depressurization, the solution was analyzed with quantitative GC using dioxane as the internal standard (HP-5 column: 60 m (Length), 0.32 mm (ID), 1.0 μm (Film)/100° C. to 225° C. in 5° C./min, 10 minutes at 225° C., 225° C. to until 280° C. in 5° C./min.). The conversion of beta-caryophyllene was 97%. The yields of (I), (II), (III), (IV) and (V) where found to be 40%, 10%, 3%, 1% and 2% respectively.

Example II.2

Oxidation of β-caryophyllene at 210° C. with N₂O (40 Bar) without Added Solvent

A 300 mL autoclave is charged with 100 g beta-caryophyllene (88 wt.-% obtained from Aldrich Chemicals) and flushed 3 times with N₂ (50 bar). The vessel is then pressurized with N₂O (40 bar) at room temperature. The magnetic stirring is turned on and the autoclave heated to the reaction temperature (210° C.) for 3 hours. During reaction the pressure in the autoclave was about 70 to 75 bar. After cooling to room temperature and slow depressurization, the solution was analyzed with quantitative GC using dioxane as the internal standard (HP-5 column: 60 m (Length), 0.32 mm (ID), 1.0 μm (Film)/100° C. to 225° C. in 5° C./min, 10 minutes at 225° C., 225° C. to until 280° C. in 5° C./min.). The conversion of beta-caryophyllene was 58% and the selectivity of (I), (II), (III) and (IV) where found to be 59%, 15%, 8% and 2% respectively. The 4R/4S-diastereomeric ratio of 1-[(1R,4R,8S)-10,10-dimethyl-7-methylene-4-bicyclo[6.2.0]decanyl]ethanone in the crude product was 64:36.

Example II.3

The crude product obtained in example II.2 was purified by means of fractional distillation using a spinning band column whereupon 1-[(1R,4R/S,8S)-10,10-dimethyl-7-methylene-4-bicyclo[6.2.0]decanyl]ethanone was obtained in a purity of 99.6%. The identity and purity of the final product was determined by means of GC (Area-% of the FID detector signal). 1-[(1R,4R/S,8S)-10,10-dimethyl-7-methylene-4-bicyclo[6.2.0]decanyl]ethanone consists of a mixture of the 4R- and 4S-diastereoisomers, wherein the 4R-isomer was found to be the major and the 4S-isomer the minor diastereoisomer. Several 4R/4S-diastereomeric ratios could be obtained with the highest one being 97/3. The relative configuration of the major isomer in this 97/3 mixture could be identified to be 1-[(1R,4R,8S)-10,10-dimethyl-7-methylene-4-bicyclo[6.2.0]decanyl]ethanone through X-Ray analyses of the 2,4-dinitrophenylhydrazone derivative thereof.

III) Analytical Characterization of 1-[(1R,4R/S,8S)-10,10-dimethyl-7-methylene-4-bicyclo[6.2.0]decanyl]ethanone The identity of 1-[(1R,4R/S,8S)-10,10-dimethyl-7-methylene-4-bicyclo[6.2.0]decanyl]ethanone was further determined using high resolution GC-MS and ¹H- and ¹³C-1D/2D-NMR.

High Resolution GC-MS:

calculated: 220.1827.

found: 220.1851 (major 4R-diastereoisomer) 220.1824 (minor 4S-diastereoisomer).

¹³C-NMR-Analysis:

1-[(1R,4R,8S)-10,10-dimethyl-7-methylene-4-bicyclo[6.2.0]decanyl]ethanone

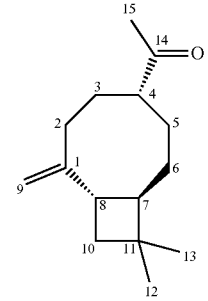

| Atom number | ¹³C shifts measured (multiplicity)¹ | ¹³C shifts calculated (multiplicity)² | ¹³C shifts literature (multiplicity)³ |
|---|---|---|---|
| 14 | 210.69 (s) | 210.7 ± 0.0 (s) | 211.58 (s) |
| 1 | 150.91 (s) | 150.9 ± 0.0 (s) | 151.66 (s) |
| 9 | 109.44 (t) | 109.4 ± 0.0 (t) | 109.61 (t) |
| 7 | 53.85 (d) | 53.9 ± 0.0 (d) | 48.35 (d) * |
| 4 | 47.69 (d) | 47.7 ± 0.0 (d) | 54.25 (d) * |
| 8 | 42.01 (d) | 42.0 ± 0.0 (d) | 42.34 (d) |
| 2 | 36.07 (t) | 36.1 ± 0.0 (t) | 35.97 (t) |
| 10 | 35.41 (t) | 36.6 ± 1.1 (t) | 36.32 (t) |
| 11 | 33.28 (s) | 33.3 ± 0.0 (s) | 33.70 (s) |
| 12 | 29.74 (q) | 29.2 ± 2.4 (q) | 22.48 (q) * |
| 15 | 28.07 (q) | 29.0 ± 0.9 (q) | 30.07 (q) |
| 6 | 26.95 (t) | 26.9 ± 0.0 (t) | 25.34 (t) |
| 3 | 24.96 (t) | 25.0 ± 0.0 (t) | 28.44 (t) * |
| 5 | 21.72 (t) | 21.7 ± 0.0 (t) | 27.33 (t) * |
| 13 | 21.43 (q) | 22.6 ± 0.0 (q) | 21.72 (q) |

¹HSQC, NOESY, DEPT and INADEQUATE pulse sequences were measured in CDCl₃ at 20° C. to secure the assignments
²Calculated with the HOSE - Code Method (Anal. Chim. Acta. 1978, Vol. 103, pp. 355-365)
³Compound 3 in Matsubara et al., Nippon Nogei Kagaku Kaishi, 1985, Vol. 59(1), pp. 19-24; peaks marked with * show a considerable deviation The ¹³C-NMR shifts measured for 1-[(1R,4R,8S)-10,10-dimethyl-7-methylene-4-bicyclo[6.2.0]decanyl]ethanone are in excellent agreement with the calculated values. Significant deviations between the data reported in the literature and the calculated/measured data from this invention cast doubts on the correctness of the structural assignment in the literature.

1-[(1R,4S,8S)-10,10-dimethyl-7-methylene-4-bicyclo[6.2.0]decanyl]ethanone

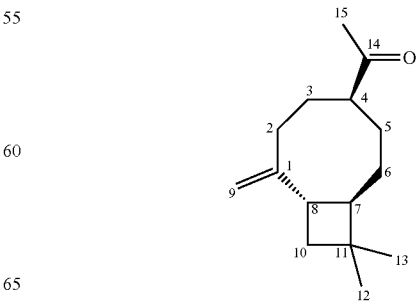

| Atom number | $^{13}$C shifts measured (multiplicity)[1] | $^{13}$C shifts calculated (multiplicity)[2] | $^{13}$C shifts literature (multiplicity)[3] |
|---|---|---|---|
| 14 | 210.69 (s) | 210.7 ± 0.0 (s) | 211.63 (s) |
| 1 | 153.86 (s) | 150.9 ± 0.0 (s) | 151.66 (s) |
| 9 | 109.16 (t) | 109.4 ± 0.0 (t) | 109.09 (t) |
| 7 | 52.75 (d) | 53.9 ± 0.0 (d) | 51.16 (d) |
| 4 | 50.81 (d) | 47.7 ± 0.0 (d) | 53.14 (d) * |
| 8 | 40.71 (d) | 42.0 ± 0.0 (d) | 48.30 (d) * |
| 2 | 40.65 (t) | 36.1 ± 0.0 (t) | 40.70 (t) |
| 10 | 33.35 (t) | 36.6 ± 1.1 (t) | 40.93 (t) * |
| 11 | 33.38 (s) | 33.3 ± 0.0 (s) | 33.63 (s) |
| 12 | 30.05 (q) | 29.2 ± 2.4 (q) | 22.60 (q) * |
| 15 | 27.87 (q) | 29.0 ± 0.9 (q) | 30.07 (q) |
| 6 | 26.95 (t) | 26.9 ± 0.0 (t) | 28.03 (t) |
| 3 | 29.27 (t) | 25.0 ± 0.0 (t) | 31.00 (t) |
| 5 | 27.69 (t) | 21.7 ± 0.0 (t) | 29.43 (t) |
| 13 | 22.56 (q) | 22.6 ± 0.0 (q) | 21.72 (q) |

[1]HSQC, NOESY, DEPT and INADEQUATE pulse sequences were measured in CDCl$_3$ at 20° C. to secure the assignments
[2]Calculated with the HOSE - Code Method (Anal. Chim. Acta. 1978, Vol. 103, pp. 355-365)
[3]Compound 4 in Matsubara et al., Nippon Nogei Kagaku Kaishi, 1985, Vol. 59(1), pp. 19-24; peaks marked with * show a considerable deviation The $^{13}$C-NMR shifts measured for 1-[(1R,4S,8S)-10,10-dimethyl-7-methylene-4-bicyclo[6.2.0]decanyl]ethanone are in excellent agreement with the calculated values. Significant deviations between the data reported in the literature and the calculated/measured data from this invention cast doubts on the correctness of the structural assignment in the literature.

IV) Scent Strip Tests

To evaluate the quality and intensity of the odor of 1-[(1R,4R/S,8S)-10,10-dimethyl-7-methylene-4-bicyclo[6.2.0]decanyl]ethanone, scent strip tests were performed with different 4R/4S-diastereoisomer ratios.

For this purpose strips of absorbent paper were dipped into solution containing 1 to 10 wt.-% 1-[(1R,4R/S,8S)-10,10-dimethyl-7-methylene-4-bicyclo[6.2.0]decanyl]-ethanone in ethanol. After evaporation of the solvent (about 30 sec.) the scent impression was olfactorically evaluated by a trained perfumer.

Scent Strip Test Results:
Odor Impression:
4R/4S=97/3: ambery, woody, musky, powdery-sweety, peppery, spicy, feminine
4R/4S=88/12: ambery, woody, tobacco, powdery-sweety, feminine
4R/4S=82/18: ambery, woody, tobacco, powdery-sweety, feminine
4R/4S=75/25: ambery, woody, tobacco, powdery-sweety, feminine
Volatility:
long lasting on blotter (>48 h)

As can be deduced from the scent strip test results, 1-[(1R,4R/S,8S)-10,10-dimethyl-7-methylene-4-bicyclo[6.2.0]decanyl]ethanone is a olfactively valuable compound.

V) Perfume Composition

An application formulation was prepared containing 1-[(1R,4R/S,8S)-10,10-dimethyl-7-methylene-4-bicyclo[6.2.0]decanyl]ethanone with a 4R/4S-diastereoisomer ratio of 97/3 (Caryophyllene Ketone F17) using the following recipe.

Application formulation for Caryophyllene Ketone F17, Pepper Pomelo F.C.2252

| Ingredient (Base): | Amount (weight parts): |
|---|---|
| Paracymene | 2 |
| Palmarosa Oil | 2 |
| Muscenone | 3 |
| Khusinyl | 3 |
| *Eucalyptus Globulus* Oil | 3 |
| Caryophyllene | 4 |
| Agrunitryl | 5 |
| Amberketal | 5 |
| Cis 3 Hexenyl Acetate | 5 |
| Ambrette F.C.56/1 | 8 |
| Gaiac Wood Oil | 10 |
| Helional | 10 |
| Dihydromyrcenol | 10 |
| Glycolierral | 12 |
| Spearmint Oil | 12 |
| Black Pepper Oil | 12 |
| Safran F.C.1936 | 12 |
| Ride Encens 50% | 15 |
| Cashmeran | 15 |
| Coumarine | 15 |
| Ambroxan | 15 |
| Sandelwood 2167/2 | 20 |
| Helvetolide | 20 |
| Patchouly Light Oil | 20 |
| Cardamome Oil | 22 |
| Vetyver Haiti Oil | 25 |
| Styrollyl Acetate | 35 |
| Tonelid | 40 |
| Ethyl Linalool | 40 |
| Ethylene Brassylate | 50 |
| Linalyl Acetate | 60 |
| Hedione | 70 |
| Methyl Pamplemousse | 70 |
| Lemon Italy Oil | 100 |
| Pentalid | 100 |
| Total (Base) | 850 |
| Caryophyllene Ketone F17 | 150 |
| Total (Formulation) | 1000 |

Description of the Odor Impression:
Right from the top note the Caryophyllene Ketone F17 wraps all the harsh and herbal notes and rounds up the evaporation of the fragrance. It provides a very subtle and linear substantiality. It also carries long during the evaporation the fresh and light top notes—holds the freshness. The material is spicy, peppery and woody. There are also aspects of leather and tobacco.

The invention claimed is:
1. A process for preparing 1-[(1R,4R/S,8S)-10,10-dimethyl-7-methylene-4-bicyclo[6.2.0]decanyl]ethanone, which comprises reacting (1R,4E,9S)-4,11,11-trimethyl-8-methylene-bicyclo[7.2.0]undec-4-ene with N$_2$O.
2. The process of claim 1, where the N$_2$O is applied at a pressure in the range of 5 to 325 bar.
3. The process of claim 1, where the molar ratio of N$_2$O to (1R,4E,9S)-4,11,11-trimethyl-8-methylene-bicyclo[7.2.0]undec-4-ene is in the range of 1:50 to 10:1.
4. The process of claim 1, where the reaction temperature is in the range of 100 to 300° C.
5. The process of claim 1, where (1R,4E,9S)-4,11,11-trimethyl-8-methylene-bicyclo[7.2.0]undec-4-ene is reacted with N$_2$O in a continuous manner.
6. The process of claim 1, further comprising the purification of the reaction mixture by distillation.

* * * * *